(12) United States Patent
Ha et al.

(10) Patent No.: US 8,475,744 B2
(45) Date of Patent: Jul. 2, 2013

(54) SOLUTION BAG FOR APPARATUS FOR CHEMICALLY ANALYZING BLOOD

(75) Inventors: Jeonghan Ha, Seoul (KR); Heejun Lee, Seoul (KR); Tae Young Kang, Seoul (KR); Jungwon Shin, Seoul (KR); Hakhyun Nam, Seoul (KR); Geun Sig Cha, Seoul (KR)

(73) Assignee: I-SENS, Inc., Seoul (KR)

( * ) Notice: Subject to any disclaimer, the term of this patent is extended or adjusted under 35 U.S.C. 154(b) by 367 days.

(21) Appl. No.: 12/739,696

(22) PCT Filed: Oct. 30, 2008

(86) PCT No.: PCT/KR2008/006431
§ 371 (c)(1),
(2), (4) Date: Apr. 23, 2010

(87) PCT Pub. No.: WO2009/057970
PCT Pub. Date: May 7, 2009

(65) Prior Publication Data
US 2010/0273248 A1   Oct. 28, 2010

(30) Foreign Application Priority Data

Nov. 1, 2007 (KR) .......................... 10-2007-0110991

(51) Int. Cl.
*A61J 1/10* (2006.01)
(52) U.S. Cl.
USPC ............. 422/555; 422/50; 422/500; 422/501; 422/502; 436/180

(58) Field of Classification Search
USPC ................. 422/555, 544, 547, 537, 538, 939, 422/944, 50, 500–502; 436/180
See application file for complete search history.

(56) References Cited

U.S. PATENT DOCUMENTS 4,745,950 A * 5/1988 Mathieu ........................ 137/798
4,805,675 A * 2/1989 Joseph et al. .................. 141/302

FOREIGN PATENT DOCUMENTS

| JP | 11-248666 A | 9/1999 |
| JP | 2003-161675 A | 6/2003 |
| JP | 2005-291840 A | 10/2005 |

* cited by examiner

*Primary Examiner* — Jyoti Nagpaul
(74) *Attorney, Agent, or Firm* — Rabin & Berdo, P.C.

(57) ABSTRACT

The present invention provides a solution bag that is used for medical treatment and stores solution used for an apparatus for analyzing blood chemistry that measures and analyzes the concentrations of electrolytes, the partial pressures of gases, and the concentrations of metabolites or the volume ratio of red blood cells contained in blood. The solution bag for an apparatus for analyzing blood chemistry of the present invention includes: a receptacle that contains a solution; a valve body that is attached to the receptacle and has a through-hole longitudinally formed therein; a valve spool that is disposed in the through-hole of the valve body; and a solution leakage preventing unit that is disposed in the valve spool, in which the valve body has a flow channel and a solution discharging pipe spaced at a predetermined distance from each other.

6 Claims, 6 Drawing Sheets

SOLUTION BAG FOR APPARATUS FOR CHEMICALLY ANALYZING BLOOD

TECHNICAL FIELD

The present invention relates to a solution bag for an apparatus for analyzing blood chemistry. More particularly, the present invention relates to a solution bag that is used for medical treatment and stores solution used for an apparatus for analyzing blood chemistry, which measures and analyzes the concentrations of electrolytes (Na+, K+, Cl−, etc.), gases (PO2, PCO2), and metabolites (glucose, lactate, urea) or the volume ratio of red blood cells contained in blood.

BACKGROUND ART

In general, the concentrations of electrolytes, the partial pressures of gases, and the concentrations of metabolites or the volume ratio of the red blood cells in blood maintain homeostasis in a human body, and when concentration imbalance occurs, various diseases are identified due to excessive or lack of concentrations thereof. Therefore, prompt measurement of the concentrations of electrolytes, the partial pressures of gases, and the concentrations of metabolites or the volume ratio of the red blood cells in blood helps a medical team quickly estimate a disorder of a human body or progress of a disease due to bionic imbalance. Equipment for measuring the concentrations of ions of electrolytes, the partial pressures of gases, and the concentrations of metabolites or the volume ratio of the red blood cells in blood may include a blood supplier that supplies blood, a sensing unit that includes a sensor, a solution supplier that supplies solution to the sensor, a data process unit, and a plurality of driving sources. The sensing unit measures a data value of the solution, which is a reference, and the concentrations of electrolytes, the partial pressures of gases, and the concentrations of metabolites or the volume ratio of the red blood cells in blood. Further, a controller corrects data values about the concentration of electrolytes, the partial pressures of gases, and the concentrations of metabolites or the volume ratio of the red blood cells in blood, on the basis of the data value obtained from the solution, thereby improving reliability of the measurement. The solution stored in a solution bag may be received in a cartridge. The solution bag storing the solution is not contaminated by outside contaminants only when being opened right before use, and reliability of the measured data is improved. Solution bags received in cartridges in the related art are opened in advance and inserted into a measuring apparatus by a user, and they do not sufficiently cope with this problem.

DETAILED DESCRIPTION

Technical Problem

The present invention has been made in an effort to provide a solution bag for an apparatus for analyzing blood chemistry having advantages of preventing in advance solution from being contaminated from outside contaminants and improving reliability of measured data by opening the solution bag when a cartridge equipped with the solution bag is attached to the main body of the apparatus for analyzing blood chemistry.

Technical Solution

An exemplary solution bag for an apparatus for analyzing blood chemistry according to an embodiment of the invention includes: a receptacle that contains a solution; a valve body that is attached to the receptacle and has a through-hole longitudinally formed therein; a valve spool that is disposed in the thorough-hole of the valve body; and a solution leakage preventing unit that is disposed in the valve spool, in which the valve body has a flow channel and a solution discharging pipe spaced at a predetermined distance from each other, and the solution leakage preventing unit of the valve spool includes a first blocking member that prevents the solution from leaking outside and a second blocking member that is spaced apart from the first blocking member and stops or allows the solution flow form the flow channel to the solution discharging pipe.

It is preferable that the valve spool is disposed to protrude from the valve body at the opposite side of the receptacle. It is preferable that the valve body has sticking-out that are fitted in a cartridge case. It is preferable that the solution discharging pipe protrudes circumferentially.

Advantageous Effects

According to this embodiment, since the valve that is opened when the cartridge is attached to the main body of the apparatus for analyzing blood chemistry is provided, it is possible to prevent the solution from being contaminated from outside contaminants and improve reliability of measured data.

BEST MODE

Hereinafter, preferred exemplary embodiments of the invention are described with reference to the accompanying drawings.

Figure 1:
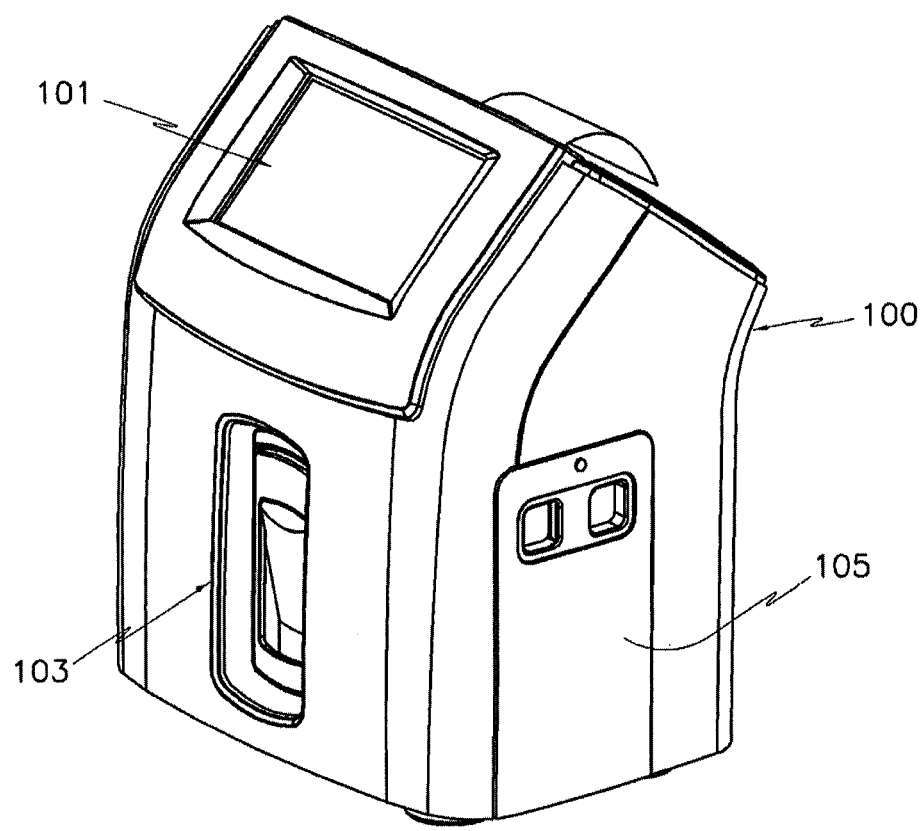
FIG. 1 is a perspective view of an apparatus for analyzing blood chemistry including an exemplary embodiment of the present invention.
Figure 2:
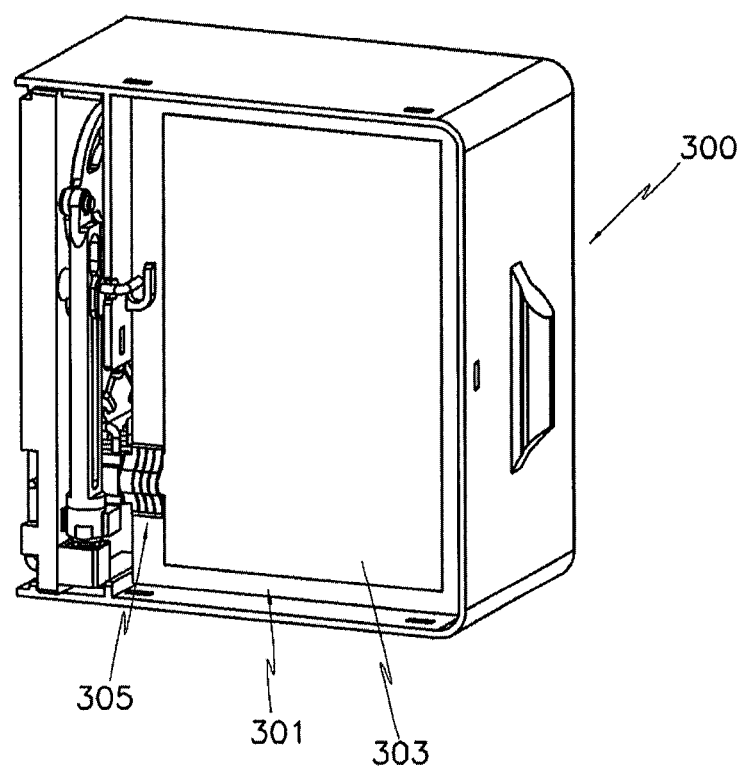
FIG. 2 is a perspective view of a cartridge that is attached to a main body of an apparatus for analyzing blood chemistry including an exemplary embodiment of the present invention.
Figure 3:
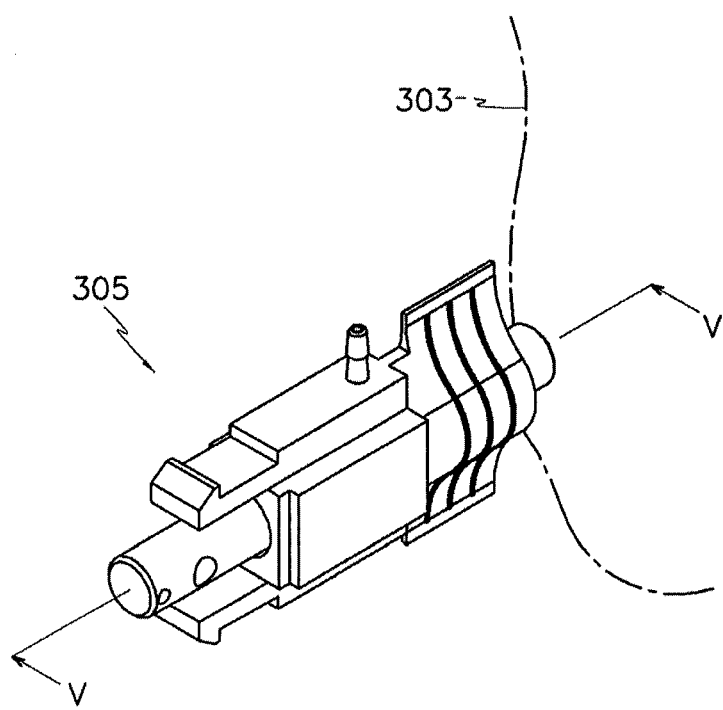
FIG. 3 is a perspective view showing in detail the main part of the present invention.
Figure 4:
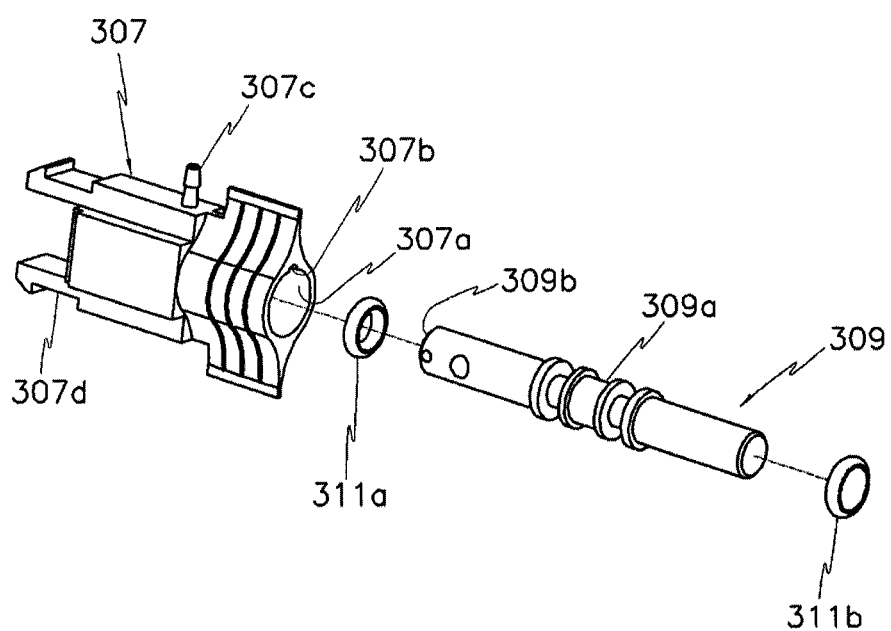
FIG. 4 is an exploded view of FIG. 3.

FIG. 1 is a perspective view of an exemplary embodiment of the present invention in a portable apparatus for analyzing blood chemistry. The portable apparatus for analyzing blood chemistry includes a main body 100 and a cartridge (300 in FIG. 2). The main body 100 of the apparatus for analyzing blood chemistry may include a display 101 and a blood introducing unit 103 on the outside, in addition to the main body 100. Further, the main body 100 of the apparatus for analyzing blood chemistry may receive the cartridge 300 in a space therein. Further, the main body 100 of the apparatus for analyzing blood chemistry may include a cartridge door 105 to separate the cartridge 300 received in the main body from the outside.

The cartridge 300 is disposed in the main body 100 of the apparatus for analyzing blood chemistry, and when measuring the concentrations of electrolytes, the partial pressures of gases, and the concentrations of metabolites or volume ratio of the red blood cells in blood, can sense the measured values from the sample blood and solution and then transmit the measured data values to a controller (not shown) provided in the apparatus for analyzing blood chemistry. The cartridge 300 includes a sensor card (not shown) that measures desired data from the sample blood and solution, and a solution bag 301 receiving the solution. The solution is transferred to the sensor card and can be used as a reference value for correcting the measured concentrations of electrolytes, the partial pressures of gases, and the concentrations of metabolites, or volume ratio of the red blood cells in blood.

The solution bag 301 includes a solution receptacle 303 that contains the solution, and a valve 305 that discharges the solution in the solution receptacle 303 to the outside. It is preferable that the solution receptacle 303 is formed of a bag made of synthetic resin or aluminum.

The valve 305 includes a valve body 307 and a valve spool 309. The valve body 307 has a hole 307a longitudinally formed through the center. Further, the valve body 307 has a flow channel 307b in a predetermined section (A) along the hole 307a to allow the solution to flow. The flow channel 307b is preferably formed from the solution receptacle 303 within the section (A). The valve body 307 has a solution discharging pipe 307c spaced at a section (B) apart from the flow channel 307b. The solution discharging pipe 307c is disposed to face the outer circumference of the valve body 307. A hose (not shown) made of synthetic resin may be combined with the solution discharging pipe 307c to transfer the solution to the sensor card, etc. The valve body 307 has sticking-out portions 307d at the front ends to be fixed to a cartridge case. The sticking-out portions 307d are formed in a common hook shape and fitted in the cartridge case.

The valve spool 309 is slidably fitted in the hole 307a of the valve body 307. The valve spool 309 has a groove 309a at a section (C). The groove 309a of the valve spool 309 is a channel through which the solution can flow. O-rings 311, that is, a solution leakage preventing unit, are disposed at both sides of the groove 309a on the valve spool 309. That is, the solution leakage preventing unit is provided with a first blocking member 311a and a second blocking member 311b at both sides of the valve spool 309. The solution leakage preventing unit, in addition to preventing the solution from leaking outside, connects the solution receptacle 303 with the solution discharging pipe 307c to discharge the solution, if needed. That is, the first blocking member 311a is always disposed outside the section (B), while the second blocking member 311b is disposed in the section (B) and moves to the section (A) such that the channel 307 is connected with the solution discharging pipe 307c when the cartridge is mounted. Further, the valve spool 309 has a protrusion 309b formed by extending the end opposite to the solution receptacle 303.

Meanwhile, a protruding block (B in FIG. 6) that pushes the protrusion 309b of the valve spool 309 is formed at the main body 100 of the apparatus for analyzing blood chemistry facing the protrusion 309b of the valve spool 309. This structure allows the solution to be used by moving the valve spool 309 when the cartridge 300 equipped with the solution bag is attached to the main body 100 of the apparatus for analyzing blood chemistry.

Figure 5:
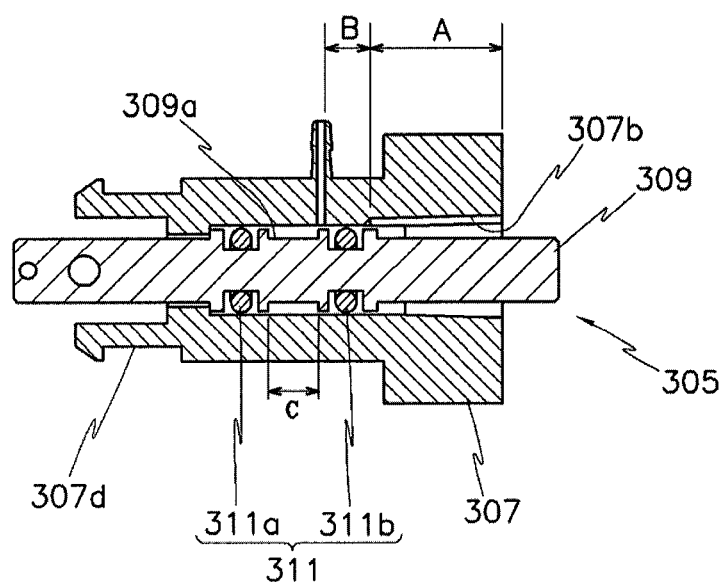
FIG. 5 is a cross-sectional view taken along the line V-V of FIG. 3.
Figure 6:
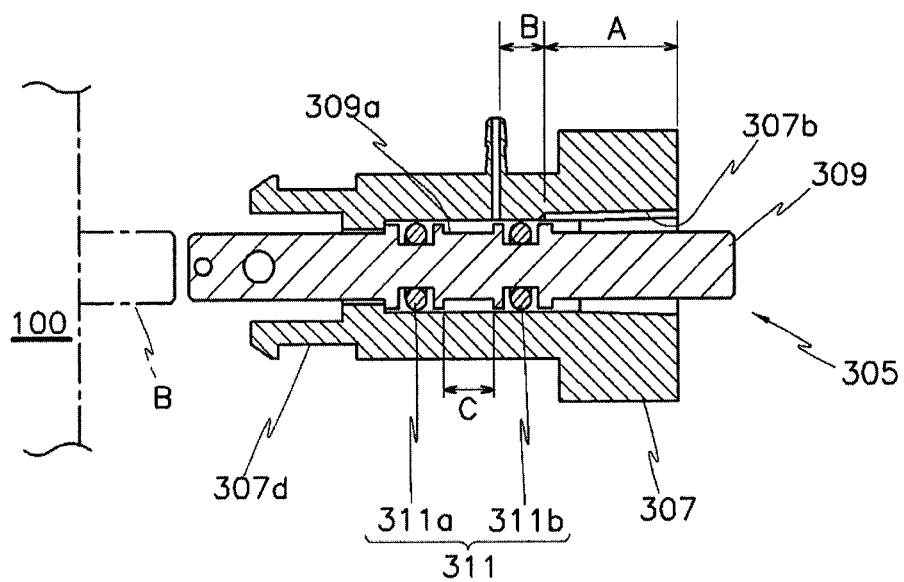
FIG. 6 is a cross-sectional view illustrating an open valve, corresponding to FIG. 5.

The operation of an exemplary embodiment of the present invention is described below. FIG. 5 is a cross-sectional view of a valve 305 before the cartridge 300 is attached to the main body 100 of the apparatus for analyzing blood chemistry, and FIG. 6 is a cross-sectional view after the cartridge 300 is attached to the main body 100 of the apparatus for analyzing blood chemistry.

In the valve 305 of the solution bag 301 before the cartridge 300 is attached to the main body 100 of the apparatus for analyzing blood chemistry, as shown in FIG. 5, the second blocking member 311b fitted on the valve spool 309 is disposed in the section (B). In this position, the second blocking member 311b is disposed in the section (B) and stops the solution from flowing to the channel 307b and the solution discharging pipe 307c. In this position, the cartridge 300 is mounted in the main body 100 of the apparatus for analyzing blood chemistry. The cartridge 300 moves to the main body 100 of the apparatus for analyzing blood chemistry (in the arrow direction in FIG. 6), and the protrusion 309b of the valve spool 309 is moved to the opposite direction of the arrow by the block (B). Accordingly, the valve spool 309 moves and the second blocking member 311b is positioned at the middle portion of the section (A). As the second blocking member 311b is positioned at the middle portion of the section (A), the channel 307b is connected with the solution discharging pipe 307c, such that the solution can be discharged. In this position, the first ring 311a still functions as a seal to prevent the solution from leaking outside.

As described above, according to an exemplary embodiment of the present invention, since the valve 305 that allows the solution to flow is opened when the disposable cartridge 300 is received in the main body 100 of the apparatus for analyzing blood chemistry, the solution is prevented from being contaminated from outside contaminants, thereby improving accuracy of data measurement.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A solution bag for an apparatus for analyzing blood chemistry, comprising:
    a receptacle that contains a solution;
    a valve body that is attached to the receptacle and has a through-hole longitudinally formed therein;
    a valve spool that is disposed in the through-hole of the valve body; and
    a solution leakage preventing unit that is disposed in the valve spool;
    wherein the valve body has a flow channel longitudinally formed along the through-hole and a solution discharging pipe perpendicularly formed at a face of the valve body, wherein the flow channel and the solution discharging pipe are spaced at a predetermined distance from each other; and
    wherein the solution leakage preventing unit of the valve spool includes a first blocking member that substantially prevents the solution from leaking outside and a second blocking member that is spaced apart from the first blocking member and selectively stops or allows the solution flow from the flow channel to the solution discharging pipe.

2. The solution bag for an apparatus for analyzing blood chemistry of claim 1, wherein the valve spool is disposed to protrude from the valve body at the opposite side of the receptacle.

3. The solution bag for an apparatus for analyzing blood chemistry of claim 1, wherein the valve body has sticking-out portions that are fitted in a cartridge case.

4. The solution bag for an apparatus for analyzing blood chemistry of claim 1, wherein the solution discharging pipe protrudes circumferentially.

5. The solution bag for an apparatus for analyzing blood chemistry of claim 1, wherein the valve spool has a groove between the first blocking member and the second blocking member to allow the solution to flow.

6. The solution bag for an apparatus for analyzing blood chemistry of claim 1, wherein each of the first blocking member and the second blocking member is an O-ring.

* * * * *